US011390907B2

(12) United States Patent
Ruvolo et al.

(10) Patent No.: US 11,390,907 B2
(45) Date of Patent: Jul. 19, 2022

(54) SYNTHESIS OF POOLS OF PROBES BY PRIMER EXTENSION

(71) Applicant: Agilent Technologies, Inc., Santa Clara, CA (US)

(72) Inventors: Michael Ruvolo, Santa Clara, CA (US); Emily Marine Leproust, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1089 days.

(21) Appl. No.: 14/772,063

(22) PCT Filed: Mar. 5, 2013

(86) PCT No.: PCT/US2013/029168
§ 371 (c)(1),
(2) Date: Sep. 1, 2015

(87) PCT Pub. No.: WO2014/137329
PCT Pub. Date: Sep. 12, 2014

(65) Prior Publication Data
US 2016/0258002 A1 Sep. 8, 2016

(51) Int. Cl.
| | |
|---|---|
| *C12P 19/34* | (2006.01) |
| *C07H 21/04* | (2006.01) |
| *C12Q 1/6811* | (2018.01) |
| *C12Q 1/6876* | (2018.01) |
| *C12Q 1/6806* | (2018.01) |
| *C12N 15/10* | (2006.01) |

(52) U.S. Cl.
CPC ........ *C12Q 1/6811* (2013.01); *C12N 15/1068* (2013.01); *C12Q 1/6806* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,518,900 A | 5/1996 | Nikiforov et al. | |
| 8,034,917 B2 | 10/2011 | Yamada | |
| 2002/0187476 A1* | 12/2002 | Koroulis | C12Q 1/6813 435/6.11 |
| 2009/0239764 A1 | 9/2009 | Sparks et al. | |
| 2010/0068701 A1 | 3/2010 | Yamada et al. | |
| 2012/0053082 A1 | 3/2012 | Barrett et al. | |

FOREIGN PATENT DOCUMENTS

| | | |
|---|---|---|
| CN | 101835903 A | 9/2010 |
| WO | WO 93/09245 | 5/1993 |
| WO | WO2011140187 A1 | 11/2011 |

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Archaea," Wikipedia.com (accessed May 11, 2016).*
"Algae," Wikipedia.com (accessed Mar. 2016).*
"Protozoa," Wikipedia.com (accessed May 11, 2016).*
"List of sequenced bacterial genomes" (Wikipedia.com; accessed Jan. 24, 2014).*
"List of sequenced animal genomes," Wikipedia.com, accessed Jan. 19, 2018. (Year: 2018).*
"Viruses", Wikipedia.com, accessed Nov. 24, 2012. (Year: 2012).*
"How many species of bacteria are there", wiseGEEK.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," (Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 2016. (Year: 2016).*
"Protozoa," Wikipedia.com, accessed May 11, 2016. (Year: 2016).*
"List of sequenced bacterial genomes", Wikipedia.com; accessed Jan. 24, 2014. (Year: 2014).*
"A human gut bacterial genome and culture collection for improved metagenomics analysis," Forster et al., Nature Biotechnology, vol. 37, Feb. 2019, pp. 186-192. (Year: 2017).*
"Psst, the human genome was never completely sequenced", Sharon Begley, Stat News, Jun. 20, 2017. (Year: 2017).*
Extended European Search Report issued for European Application No. 13876980.7, dated Sep. 28, 2016.

* cited by examiner

*Primary Examiner* — Bradley L. Sisson (57) ABSTRACT

Provided herein is a method for making a pool of probes by primer extension. In certain embodiments, the method comprises hybridizing a first population of oligonucleotides comprising a top strand sequence having the following formula V1-B-3' with a second population of oligonucleotides comprising a bottom strand sequence having the following formula V2'-B'-3' to provide a population of duplexes. After hybridizing, the 3' ends of the oligonucleotides in the duplexes are extended to produce a population of double stranded products comprising a top strand sequence having the following formula V1-B-V2, where V2 is complementary to V2'.

20 Claims, 8 Drawing Sheets

SYNTHESIS OF POOLS OF PROBES BY PRIMER EXTENSION

BACKGROUND

Chromosomal rearrangements, deletions, and other aberrations have long been associated with genetic diseases. Structural abnormalities in chromosomes often arise from errors in homologous recombination. Structural abnormalities can occur in gametes and therefore will be present in all cells of an affected person's body, or they can occur during mitosis and give rise to a genetic mosaic individual who has some normal and some abnormal cells.

There is an ongoing need to develop efficient ways to make probes for use in genomics, particular in the detection and analysis of chromosomal abnormalities.

SUMMARY

Provided herein is a method for making a pool of probes by primer extension. In certain embodiments, the method comprises hybridizing a first population of oligonucleotides comprising a top strand sequence having the following formula $V_1$-B-3' with a second population of oligonucleotides comprising a bottom strand sequence having the following formula $V_2'$-B'-3' to provide a population of duplexes. In these embodiments, the nucleotide sequences of B and B' are complementary and are at least 15 nucleotides in length, the nucleotide sequence of B is the same for each oligonucleotide of the first population, the nucleotide sequence of B' is the same for each oligonucleotide of the second population, the nucleotide sequence of $V_1$ is variable between the oligonucleotides of the first population, the nucleotide sequence of $V_2'$ is variable between the oligonucleotides of the second population, and $V_1$ and $V_2'$ hybridize to different sites a reference genome. After hybridizing, the 3' ends of the oligonucleotides in the duplexes are extended to produce a population of double stranded products comprising a top strand sequence having the following formula $V_1$-B-$V_2$, where $V_2$ is complementary to $V_2'$.

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example. In certain cases, a population of oligonucleotides can be made by fabricating an array of the oligonucleotides using in situ synthesis methods, and cleaving oligonucleotides from the substrate. Examples of such methods are described in, e.g., Cleary et al (Nature Methods 2004 1: 241-248) and LeProust et al (Nucleic Acids Research 2010 38: 2522-2540).

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "complementary" as used herein, means that two nucleic acids, e.g., DNA or RNA, contain a series of consecutive nucleotides which are capable of forming matched Watson-Crick base pairs to produce a region of double-strandedness (except in the region of mismatch). Thus, adenine in one strand of nucleic acid pairs with thymine in an opposing complementary DNA strand or with uracil in an opposing complementary RNA strand, and guanine in one nucleic acid strand pairs with cytosine in an opposing nucleic acid strand. The region of pairing is referred to as a "duplex." Alternatively, two nucleic acid molecules are said to be "complementary" if they can hybridize to one another with sufficient stability to permit them to remain annealed to one another under at least conventional "low stringency" conditions. Thus, two complementary molecules need not exhibit precise complementarity, but need only be sufficiently complementary in sequence to be able to form a stable double-stranded structure. Departures from complete complementarity are therefore permissible, as long as such departures are not sufficient to completely preclude hybridization to form a double-stranded structure.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., at least 5 or 10 times, up to 30 or 40 or more times) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10} [Na^+])+0.41$ (fraction G+C)–(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

A "binding site" for an oligonucleotide refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a "top" or "bottom" strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "denaturing," as used herein, refers to the separation of at least a portion of the base pairs of a nucleic acid duplex by placing the duplex in suitable denaturing conditions.

Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A–T base pairs may separate while regions enriched for G–C base pairs may remain paired.) Nucleic acid may also be denatured chemically (e.g., using urea or NaOH).

The term "extending", as used herein, refers to the extension of a primer by the addition of nucleotides using a polymerase. If a primer that is annealed to a nucleic acid is extended, the nucleic acid acts as a template for extension reaction.

The term "circularizing", as used herein, refers to the ligation of one or more linear molecules to make a strand that is in the form of a closed circle that has no free 3' or 5' ends.

The term "unique sequence", as used herein, refers to nucleotide sequences that are different from one another, or their complements. For example, a first unique sequence has a different nucleotide sequence than a second unique sequence or its complement. Unless otherwise indicated, a unique sequence is only present in one polynucleotide in a sample.

The term "do not hybridize to each other", as used herein in the context of nucleic acids that do not hybridize to each other, refers to sequences that been designed so that they do not anneal to one another under stringent conditions. Examples of such sequences are called "sequence tokens" in certain publications, are described in, e.g., US20070259357 and Brenner et al (Proc. Natl. Acad. Sci. 1992 89:5381-3), which are incorporated by reference herein.

The term "immediately adjacent", in the context of two nucleotides that are immediately adjacent to one another, means that there are no intervening nucleotides between two nucleotides. Nucleotides that are immediately adjacent to one another can be ligated to one another.

The term "similar to one another" in the context of a polynucleotide or polypeptide, means sequences that are at least 70% identical, at least 80% identical, at least 90% identical, or at least 95% identical, to one another.

The term "single stranded" refers to a nucleic acid strand that is present in a composition in single stranded form, not in double stranded form. In certain cases, a single stranded polynucleotide may be present in a composition in the absence of any complementary polynucleotide. In other cases, e.g., in cases in which a double stranded nucleic acid has been denatured not renatured, a single stranded polynucleotide may be present in a composition that also contains a complementary polynucleotide. However, in these cases, the polynucleotides are not base paired with one another.

The term "the same", in the context of two or more sequences that are the same, refers to two or more nucleic acids that have the same sequence of nucleotides. In other words, if all the polynucleotides of a population have the same sequence, then all of the polynucleotide molecules of the population have the same sequence of nucleotides.

The term "contacting" means to bring or put together. As such, a first item is contacted with a second item when the two items are brought or put together, e.g., by touching them to each other or combining them in the same solution. Thus, a "contacted sample" is a test chromosome onto which oligonucleotide probes have been hybridized.

The term "genotyping", as used herein, refers to any type of analysis of a nucleic acid sequence, and includes sequencing, polymorphism analysis, e.g., SNP analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of a oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population. The term "variable" means that the sequences varies between the different molecules of the population, and there may be duplicates of any particular sequence.

The term "reference genome" as used herein refers to a genome to which results obtained from a test genome can be compared. In certain cases, the region under study may be of known nucleotide sequence in a reference gene, e.g. the sequence may have been deposited at NCBI's Genbank database or other database, for example. In many embodiments, the test and reference genomes are genomes from the same (e.g., mammalian) species.

The term "chromosomal rearrangement," as used herein, refers to an event where one or more parts of a chromosome are rearranged within a single chromosome or between chromosomes. In certain cases, a chromosomal rearrangement may reflect an abnormality in chromosome structure. A chromosomal rearrangement may be an inversion, a deletion, an insertion or a translocation, for example.

The term "breakpoint", in the context of a chromosomal rearrangement, refers to a junction created by a chromosomal rearrangement. For example, if there is a rearrangement between chromosome 1 and chromosome 2, the breakpoint of the rearrangement is defined by the junction of the sequence from chromosome 1 and the sequence from chromosome 2 in the rearranged chromosome.

The following description explains the formulas used in this disclosure. Certain polynucleotides described herein may be referred by a formula (e.g., "$V_1$-B-3'", "$V_2$'-B'-3'" and "$V_1$-B-$V_2$"). Such formulas follow the established convention in that they describe a polynucleotide that is oriented in the 5' to 3' direction. The components of the formula, e.g., "$V_1$", "B" and "$V_2$" refer to separately definable sequences of nucleotides within a polynucleotide, where the sequences are linked together covalently such that a polynucleotide described by a formula is a single molecule. The components of the formula may be immediately adjacent to one another or spaced from one another in the single molecule. By convention, the complement of a sequence shown in a formula will be indicated with a prime (') such that the complement of sequence "$V_2$" will be "$V_2$'". Moreover, unless otherwise indicated (e.g., if the formula is followed by a "3'-" such as in the case of "$V_1$-B-3'" or $V_2$'-B'-3'" or if the formula is preceded with "5'-"), a polynucleotide defined by a formula may have additional sequence at its 3' end, its 5' end or both the 3' and 5' ends. Other definitions of terms may appear throughout the specification. In the context of a formula, the term nucleic acid sequence refers to the sequence of nucleotides of a component of the formula. For example, the phrase "nucleic acid sequence B" refers to the sequence of nucleotides of component B.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods

Figure 1:
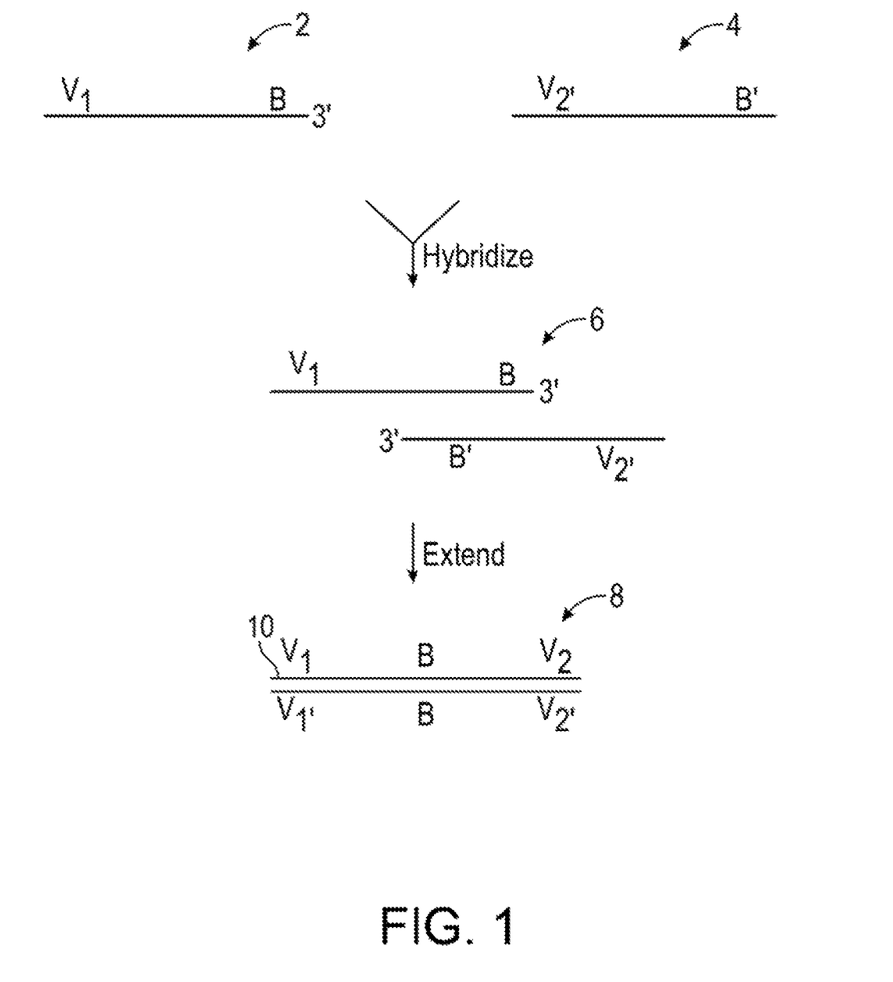
FIG. 1 schematically illustrates some of the general principles of one embodiment of the subject method.

The general principles of the subject method are illustrated in FIG. 1. In certain embodiments, this method comprises: hybridizing a first population of oligonucleotides 2 comprising a top strand sequence having the following formula $V_1$-B-3' with a second population of oligonucleotides 4 comprising a bottom strand sequence having the following formula $V_2'$-B'-3' to provide a population of duplexes 6 in which the B and B' sequences hybridize to one another and the $V_1$ and $V_2'$ sequences remain single stranded. In this embodiment, the first and second populations of oligonucleotides are characterized in that i. the nucleotide sequences of B and B' are complementary and are at least 15 nucleotides in length (which allows the first and second populations of oligonucleotides) to hybridize; ii. the nucleotide sequence of B is not variable, i.e., is the same for each oligonucleotide of the first population and the nucleotide sequence of B' is not variable, i.e., is the same for each oligonucleotide of the second population; iii. the nucleotide sequence of $V_1$ is variable between the oligonucleotides of the first population; iv. the nucleotide sequence of $V_2'$ is variable between the oligonucleotides of the second population, and v. $V_1$ and $V_2'$ hybridize to different sites in a reference genome. B and B' do not hybridize to the reference genome. After the duplexes 6 are produced, the 3' ends of the oligonucleotides in the duplexes are extended to produce a population of double stranded products 8 comprising a top strand sequence 10 having the following formula $V_1$-B-$V_2$.

As would be apparent from FIG. 1, $V_1$ is complementary to $V_1'$ and $V_2$ is complementary to $V_2'$. The resulting population of products have a top strand of the following formula $V_1$-B-$V_2$ where (i) the nucleic acid sequence B is the same for each of the top strands; (ii) the nucleic acid sequence $V_1$ varies from molecule to molecule in the population; (iii) the nucleic acid sequence $V_2$ varies from molecule to molecule in the population; and (iv) within each product, the $V_1$ and $V_2$ sequences hybridize to different sites in a reference genome. In certain embodiments, only one round of primer extension need be performed in the extension step. In other embodiments, several (e.g., 2 3, 4, or 5 or more) rounds of primer extension (where each round of primer extension comprises denaturation, reannealing of the primers, and primer extension) may be done. In some cases, the extension comprises less than 10 rounds of primer extension.

Figure 2:
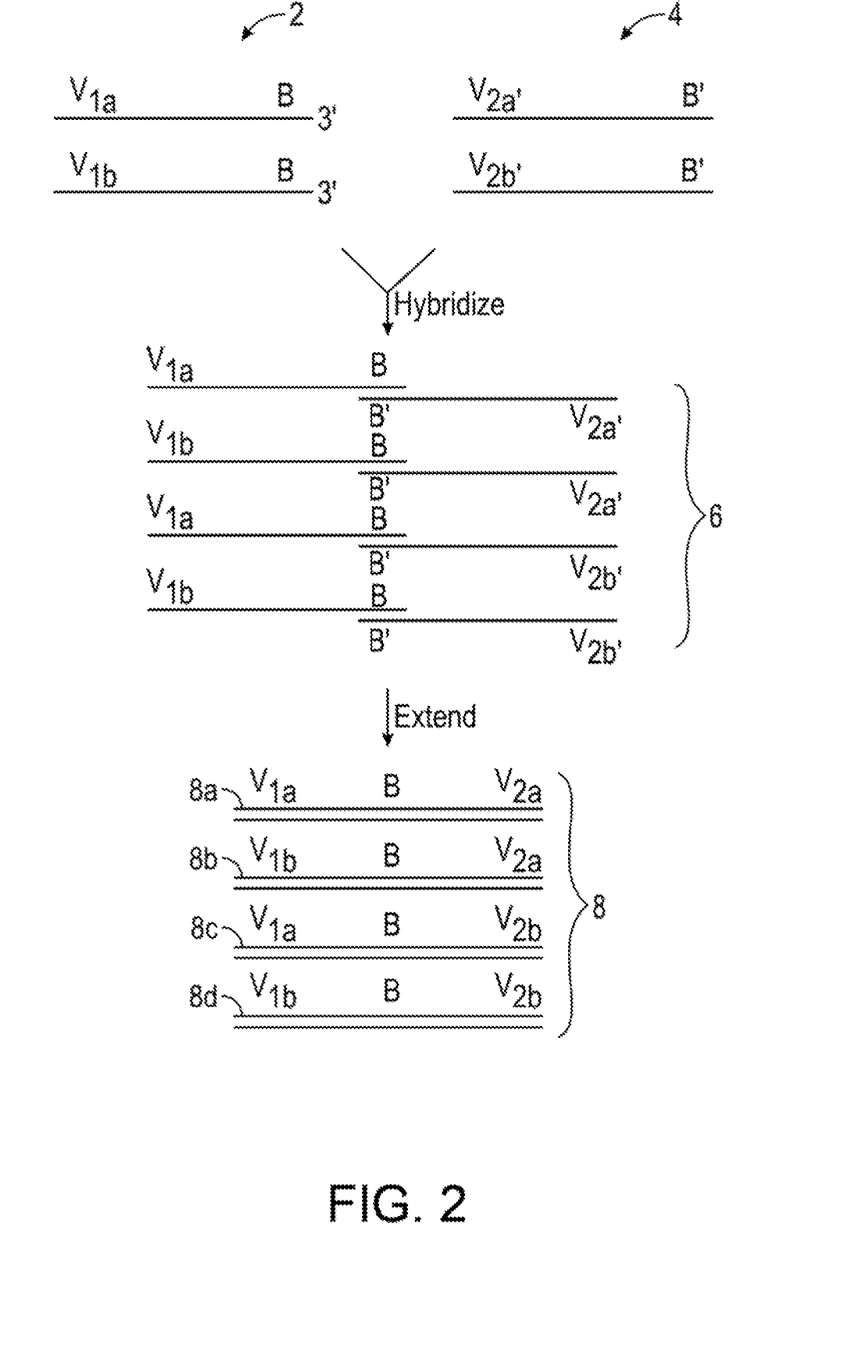
FIG. 2 schematically illustrates further principles of one embodiment of the subject method.

Some principles of the method are shown in FIG. 2. In this embodiment, the first population of oligonucleotides 2 comprises two oligonucleotides that contain different $V_1$ sequences ($V_{1a}$ and $V_{1b}$) and the same sequence B, and the second population of oligonucleotides 4 comprises two oligonucleotides that contain different $V_2'$ sequences ($V_{2a}'$ and $V_{2b}'$) and the same sequence B'. The first and second populations of oligonucleotides are hybridized together in a way that combines each of first oligonucleotides with each of the second oligonucleotides in a pairwise manner to produce a population of duplexes 6. As shown, the population of duplexes 6 contains four duplexes, each of which represents a different combination of first and second oligonucleotides, hybridized together via their B/B' sequences. The duplexes are then extended to produce a population of double stranded products 8, where each of the products has a different top strand. Specifically, as shown, the first double stranded product 8a has a top strand that has a combination of $V_{1a}$ and $V_{2a}$ sequences, the second double stranded product 8b has a top strand that has a combination of $V_{1b}$ and $V_{2a}$ sequences, the third double stranded product 8c has a top strand that has a combination of $V_{1a}$ and $V_{2b}$ sequences, and the fourth double stranded product 8d has a top strand that has a combination of $V_{1b}$ and $V_{2b}$ sequences.

In certain cases, within the product molecules, the $V_1$ and $V_2$ sequences hybridize to sites in reference genome that are separated by a distance that makes it difficult or impossible to routinely obtain a product by polymerase chain reaction. In any one first oligonucleotide molecule, the $V_1$ and $V_2$ sequences may hybridize to the long and short arm of the same chromosome, respectively, or vice versa. In other embodiments, in any one product molecule, the $V_1$ and $V_2$ sequences may hybridize to different chromosomes (e.g., the $V_1$ sequence may hybridize to chromosome 1 and the $V_2$ sequence may hybridize to chromosome 2). In other cases, the sites to which $V_1$ and $V_2$ hybridize are at least 10 kb apart in a reference genome although, in certain embodiments, this distance may be shorter, e.g., at least 2 kb or at least 5 kb. In certain cases, within each first oligonucleotide, the sequences to which $V_1$ and $V_2$ hybridize may be at least 20 kb, at least 50 kb, at least 100 kb, or at least 500 kb apart in the reference genome.

In certain cases, the $V_1$ and $V_2'$ sequences may be designed so that the $V_1$ and $V_2$ sequences in the product molecule hybridize immediately next to restriction sites in the reference genome. Sequences $V_1$, B and $V_2$ are each at least 15 nucleotides in length. In some embodiments, sequences $V_1$, B and $V_2'$ may independently be at least 18 nucleotides in length, at least 20 nucleotides in length, at least 25 nucleotides in length, at least 30 nucleotides in length, up to 50 nucleotides in length or more. As would be apparent, the sequences of $V_1$ and $V_2'$ vary independently from one another.

In certain cases, the oligonucleotides of the first population of oligonucleotides may be designed such that the $V_1$ sequences of the population hybridize to sites that are all in one strand in a first region in a reference genome (e.g., at sites that are distributed throughout, e.g., tiled through, a 50 kb or 100 kb region), and the $V_2'$ sequences of the oligonucleotides of the second population of oligonucleotides population hybridize to sites that are all in one strand in a second region in the reference genome (e.g., at sites that are distributed throughout, e.g., tiled through, a 50 kb or 100 kb region). In certain cases, the first and second regions may be known to rearrange with one another in other genomes.

Figure 3:
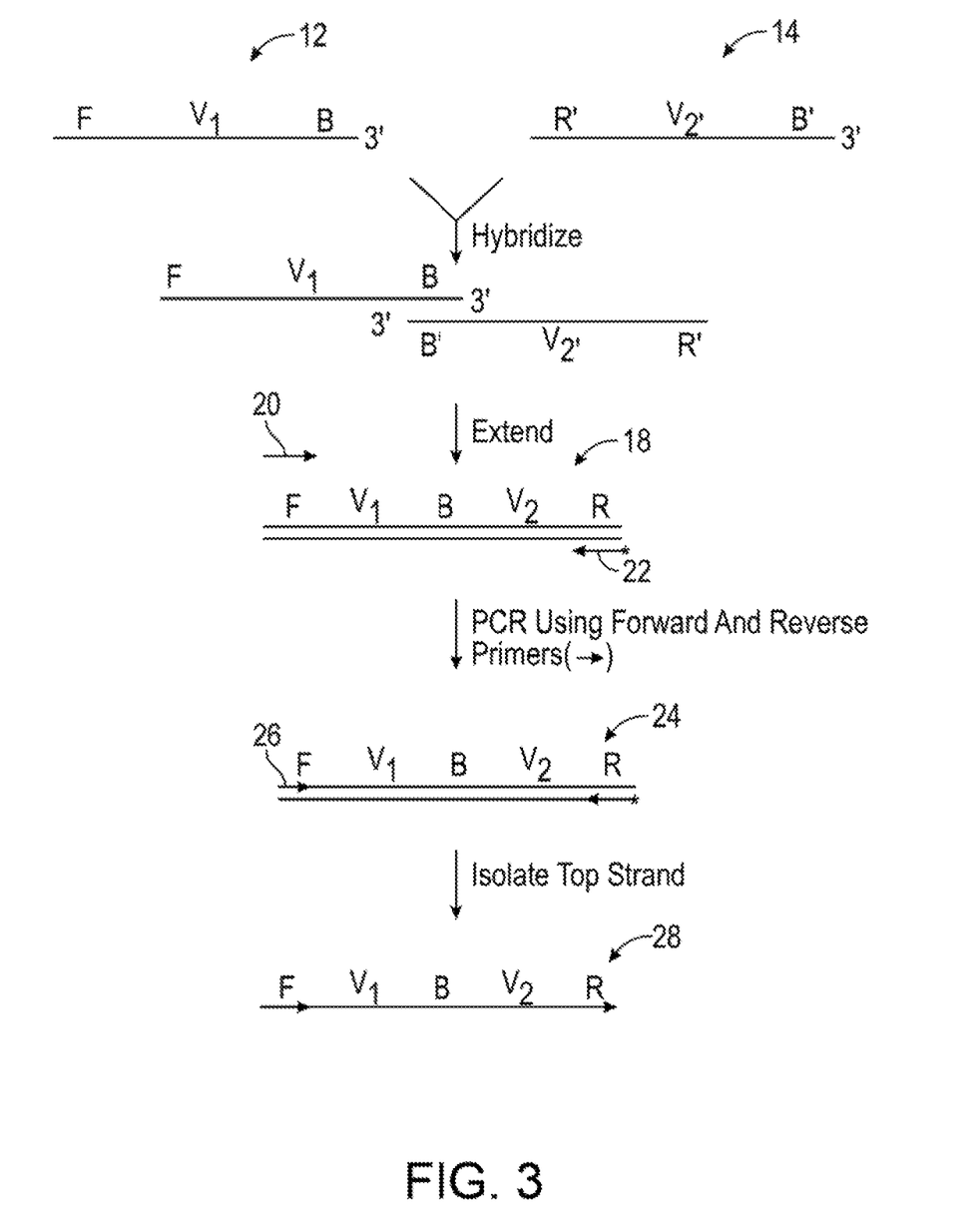
FIG. 3 schematically illustrates how the subject method can be employed to make single stranded probes.

In some embodiments and as shown in FIG. 3, the first population of oligonucleotides 12 may comprise a top strand sequence having the following formula F-$V_1$-B-3', the second population of oligonucleotides 14 may comprise a bottom strand sequence having the following formula R'-$V_2'$-B'-3' and the population of double-stranded products may comprise a top strand 18 having the following formula F-$V_1$-B-$V_2$-R, where R and the complement of F (i.e., F') provide binding sites for forward primer 20 and reverse primer 22. As shown, this method may further comprise PCR amplifying the population of double-stranded products 18 using the forward primer 20 and reverse primer 22 to produce a population of double-stranded PCR products 24 that comprise a top strand 26 sequence having a top strand of formula F-$V_1$-B-$V_2$-R.

Figure 4:
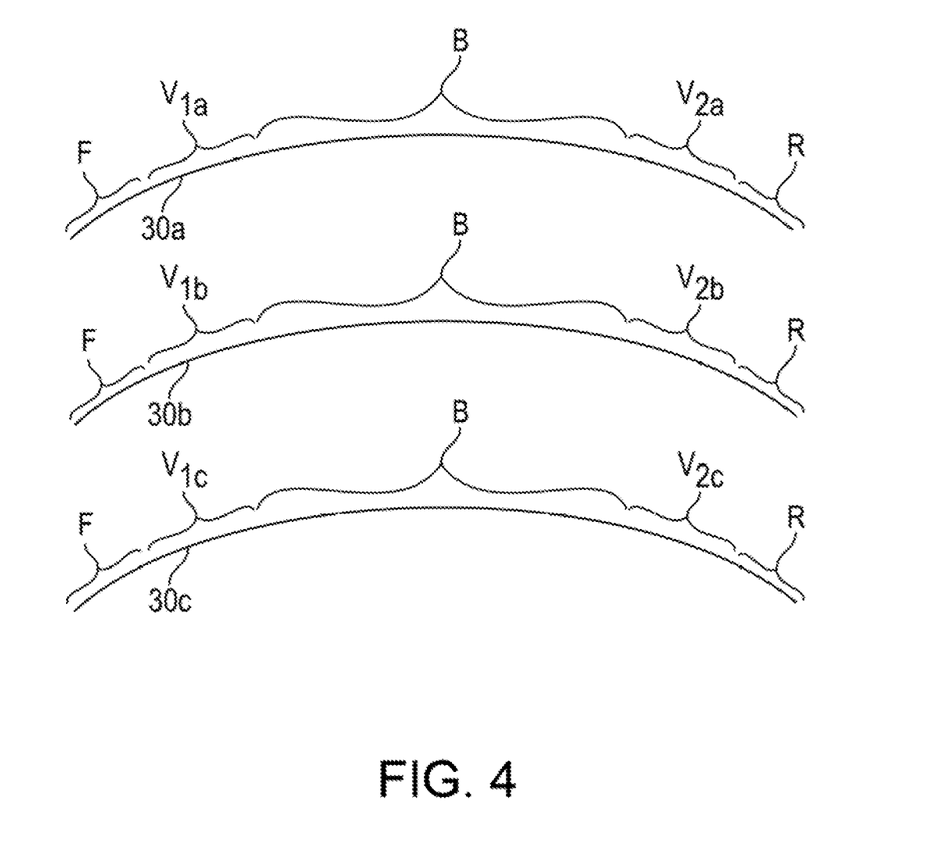
FIG. 4 schematically illustrates some of the features of the single stranded products produced by the subject method.

Prior to use, the population of double-stranded PCR products 24 may in certain cases be processed to produce a population of single-stranded products 28 of formula F-$V_1$-B-$V_2$-R. This may be done, for example, using a reverse primer that is 5'-phosphorylated (indicated by an asterisk in reverse primer 22) and a forward primer that is not 5' phosphorylated, then producing the single-stranded product by degrading the bottom strand of the population of double-stranded products using an exonuclease that selectively degrades 5'-phosphorylated nucleic acid. λ exonuclease is an example of such an enzyme, although others exist. In an alternative embodiment, the reverse primer may be biotinylated, and the bottom strands of double-stranded PCR products 24 can be removed by denaturing the double stranded product and binding the biotinylated bottom strands to streptavidin, for example. FIG. 4 illustrates a population containing three exemplary single stranded products (single stranded products 30*a*, 30*b* and 30*c*) that are made by this method. As shown in FIG. 4, the nucleic acid sequence B is the same for each of the single stranded products and hybridizes with the one or more second oligonucleotides (not shown). In the molecules shown, the 5' ends of the single stranded products 30*a*, 30*b* and 30*c* have different sequences $V_{1a}$, $V_{1b}$ and $V_1$, respectively and the 3' ends of the first oligonucleotides 30*a*, 30*b* and 30*c* have different sequences $V_{2a}$, $V_{2b}$ and $V_{2c}$, respectively.

The lengths of the various regions of the oligonucleotides in the first and second populations of oligonucleotides may vary greatly depending upon the desired application and how much freight (i.e., how many primer binding sites, molecular barcodes, etc.) is contained in the oligonucleotides. For example, as will be described below, in certain cases the B region may provide sites for at least a pair of PCR primers and, optionally, one or more molecular barcodes. In certain embodiments, nucleotide sequence of B is at least 15 bases in length, e.g., 20 to 100 bases in length or 30 bases to 60 bases in length, and the sequences of $V_1$ and $V_2'$ may be at least 10 nucleotides in length, e.g., 10 to 100 bases or 15 to 50 bases in length.

The number of members in each of the first and second populations of oligonucleotides may vary greatly depending on how the method is being performed. In some embodiments, the first and second populations of oligonucleotides may contain at least 10, at least 50, at least 100, at least 200, at least 500, or at least 1,000 and up to 10,000 or more members. Further, any one assembly may contain multiple pairs of populations of oligonucleotides that hybridize via different B sequences. For example, a third and fourth populations of oligonucleotides that hybridize via sequence $B_2$ can be assembled in the same reaction as a first and second populations of oligonucleotides that hybridize via sequence $B_1$. The method described above may be done using at least 1, at least 2, at least 5, at least 10 or at least 100 or more pairs of oligonucleotide populations, where each population hybridizes to the other population in a pair.

Figure 5A:
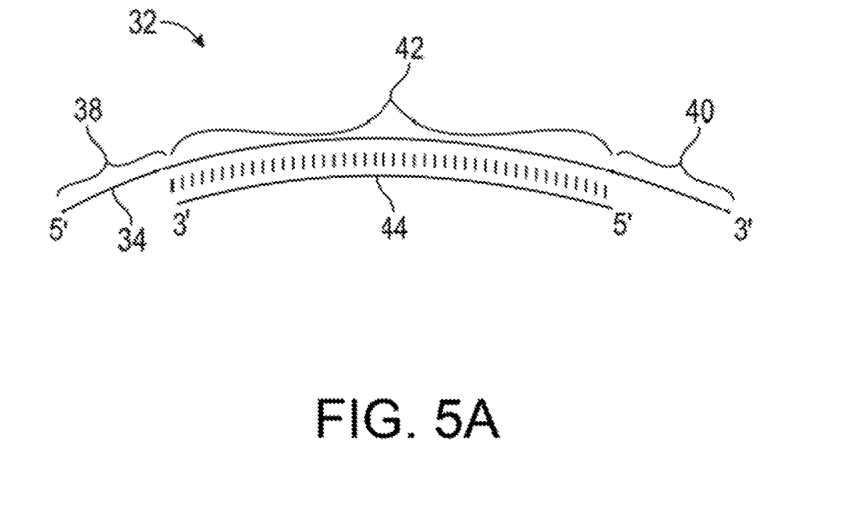
FIG. 5 schematically illustrates two types of halo probe.
Figure 5B:
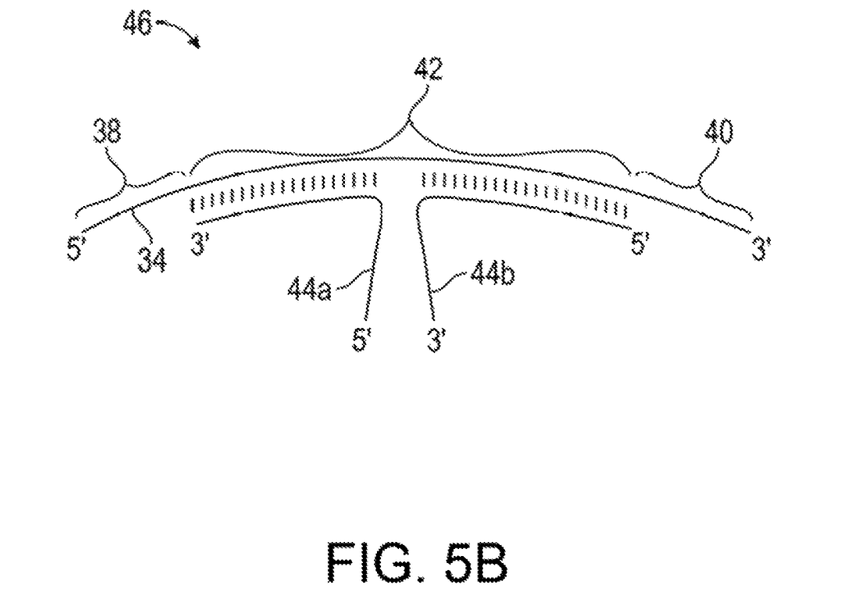

The population of single-stranded products 26 finds use as first oligonucleotides in a multiplex halo assay, where, in the context of this disclosure, a multiplex halo assay uses a population of first oligonucleotide of the formula $V_1$-B-$V_2$ (which, optionally, can contain non-hybridizing sequences 5' of the $V_1$ region and non-hybridizing 3' of the $V_2$ region) and one or more second oligonucleotides that hybridize to region B. For reference purposes, two embodiments of a halo probe, 32 and 46 are shown in FIG. 5. As illustrated in FIG. 5, both embodiments of halo probe 32 and 46 comprise: a first oligonucleotide 34 comprising flanking sequences 38 and 40 that hybridize to different regions in a fragment target DNA, and a central sequence 42. Flanking sequence 38 corresponds to the region referred to as "$V_1$" herein, flanking sequence 40 corresponds to the region referred to as "$V_2$" herein, and central sequence 42 corresponds to the region referred to as "B" herein. As shown, a halo probe further contains one or more second oligonucleotides that are complementary to central sequence 42 of the first oligonucleotide. In the context of this disclosure, these oligonucleotides can be referred to as one or more second oligonucleotides that hybridize to nucleic acid sequence B. In embodiment 32 (shown in panel A) the one or more second oligonucleotides can be a single oligonucleotide 44. In embodiment 46 (shown in panel B) the one or more second oligonucleotides can be two oligonucleotides 44*a* and 44*b*, which each contain a region that hybridizes to the first oligonucleotide, and a tail that does not hybridize to the first oligonucleotide. In certain embodiments, the one or more second oligonucleotides can provide amplification and/or sequencing primer binding sites, and, optionally, a molecular barcode sequence. These sequences may be present in the tails of oligonucleotides 44*a* and 44*b* if halo probe 46 is used.

In certain embodiments, the first oligonucleotide and the one or more second oligonucleotides so that they can hybridize with a restriction fragment of a genome to produce a complex in which at least one of the ends of at least one of the one or more second oligonucleotides is ligatably adjacent to one of the ends of the fragment, as described in U.S. Pat. No. 7,883,849 and Dahl et al. (Nucl. Acids. Res. 2005 33: e71), which are incorporated by reference herein.

Consistent with the above, the double stranded region of the halo probe may be of 15 to 100 base pairs (e.g., 30 bp to 60 bp) in length, and the sequences of the flanking regions 38 and 40 (which specifically hybridize to a target sequence in a genome) may be of 10 to 100 bases (e.g., 12-50 bases) in length. As should be readily apparent, the nucleotide sequence of the double stranded region of the halo probe should be designed to that it does not hybridize to the genome under study. The method described above may be used to make a population of first oligonucleotides that can be used in either embodiment shown in FIG. 5.

Figure 6:
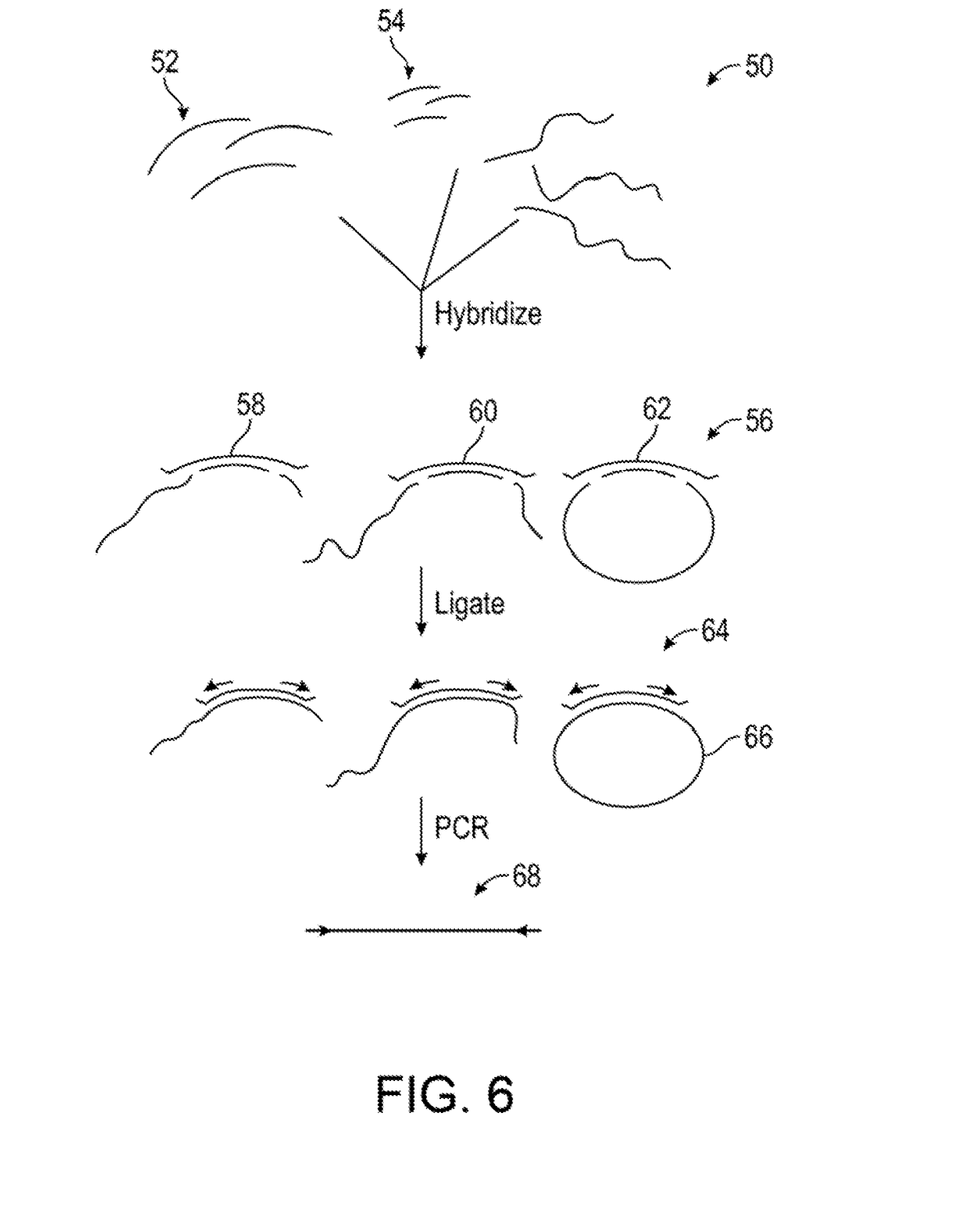
FIG. 6 schematically illustrates how the product of the subject method can be used in genome analysis.

FIG. 6 illustrates an exemplary multiplex halo assay in which the subject population of single stranded products 28 (as illustrated in FIG. 3) can be employed. Certain embodiments of the method may comprise (a) hybridizing fragmented genomic DNA 50 from a test genome with the population of first oligonucleotides 52 in the presence of one or more second oligonucleotides 54 to produce a hybridization product 56. As shown, the hybridization product contains a number of complexes, e.g., 58, 60 and 62. As shown, many of the first oligonucleotides, e.g., those in complexes 58 and 60, are hybridized to two distinct genomic fragments, which may be expected because, within each first oligonucleotide molecule, the $V_1$ and $V_2$ sequences may hybridize to sites in a genome that are distanced by at least 10 kb. In certain cases, the test genome may have a chromosomal rearrangement relative to the reference genome that effectively moves a $V_1$-complementary sequence to a site that is both proximal to and on the same strand as $V_2$-complementary sequence. In these cases, if a first oligonucleotide contains $V_1$ and $V_2$ sequences that are complementary to the sequences moved into proximity by the rearrangement, complex 62 that comprises a single genomic fragment that is hybridized to both ends of a first oligonucleotide is produced. As described above, in certain embodiments the first oligonucleotides are designed so that the $V_1$ and $V_2$ sequences are next to cleavage sites for a restriction enzyme in the reference genome. In these embodiments, the ends of the fragment in complex 62 may be ligatably adjacent to the ends of the second oligonucleotide of the complex. In other embodiments, the ends of the fragment can be trimmed back using, e.g., an exonuclease and/or flap endonuclease, to provide a complex in which the ends of the fragment are ligatably adjacent to the ends of the second oligonucleotide in the complex.

After hybridization, hybridization products 56 are contacted with a ligase in order to join the ends of the fragmented genomic DNA to the one or more second oligonucleotides to produce ligation products 64. As shown, in complexes that contain a single fragment that is hybridized to both ends of a first oligonucleotide, both ends of the fragment ligate to the one or more second oligonucleotides. In the embodiment shown (which employs a halo probe shown in panel A of FIG. 1), ligation produces circular nucleic acid molecule 66. In embodiments that employ the halo probe illustrated in panel B of FIG. 5, the genomic fragment becomes ligated two different oligonucleotides (e.g., 44a and 44b, as illustrated in panel B of FIG. 5), which effectively adds an adaptor to both ends of a genomic fragment.

After ligation, the ligation products 64 are subjected to polymerase chain reaction conditions using amplification primers that hybridize to sites that are provided by the one or more second oligonucleotides, where as noted above, if an oligonucleotide provides a binding site for a primer, then the primer may hybridize to that oligonucleotide or its complement. Exemplary sites of the amplification primers are indicated using arrows in FIG. 6. Equivalent binding sites can be provided by the alternative second oligonucleotides illustrated in panel B of FIG. 5. Production of product 68 by the amplification step indicates that the test genome contains a chromosomal rearrangement relative to the reference genome. If there is no rearrangement that brings a $V_1$-complementary sequence to a site that is both proximal to and on the same strand as $V_2$-complementary sequence, then no amplification product will be obtained.

In certain embodiments, the method may further comprise sequencing the amplification product 68. This sequencing can done using primers that hybridize to the complementary strand of the one or more second oligonucleotides. This method may be analyzed to identify the breakpoint for the chromosomal rearrangement.

As would be apparent, in certain embodiments, the sequences added by the one or more second oligonucleotides may contain sequences that are compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The sequences may be present in the one or more second oligonucleotides (either in their tails or in the sequence that hybridizes to the first oligonucleotide). In certain cases, the one of more second oligonucleotides may contain two sets of primer binding sites, one for amplifying the circular DNA by inverse PCR, and the other for sequencing the resultant product. The one of more second oligonucleotides may also contain a molecular barcode, positioned downstream of the amplification and sequencing primer binding sites, that can be used to identify from which sample a sequence is derived, or to count how many different starting molecules have been sequenced.

In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

In particular embodiments, the fragmented genomic DNA may be made by digesting genomic DNA using a restriction enzyme, e.g., one or more restrictions that have a four, five or six base pair recognition site. Alternatively, the genomic DNA may be produced from genomic DNA using chemical, physical or transposase-catalyzed fragmentation methods, see, e.g., Adey et al (Genome Biology 2010, 11:R119). For example, the physical fragmentation methods may include sonication, nebulization, or shearing of genomic DNA. In certain embodiments, prior to performing the method, the genomic DNA may be fragmented to an average size in the range of 100 bp to 10 kb, e.g., 200 bp to 1 kb.

The method described above may be used to analyze a genome from any nucleic acid-containing entity, e.g., any organism, phage or virus, etc). In certain cases the method may be used to analyze a genome from any organism, e.g., plants, animals (e.g., reptiles, mammals such as humans and mice, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human. In one embodiment, the test genome is suspected of containing a chromosomal rearrangement.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. In addition, the reaction may be multiplex such that a plurality of different target loci (e.g., 10 to 1000) are targeted in a single reaction.

Compositions

A composition comprising a population of duplexes is provided. In certain embodiments, the duplexes comprise: a first population of oligonucleotides comprising a top strand sequence having the following formula $V_1$-B-3'; and a second population of oligonucleotides comprising a bottom strand sequence having the following formula: $V_2'$-B'-3', as described above. In some embodiments, the nucleotide sequences of B and B' are complementary and are at least 15 nucleotides in length; the nucleotide sequence of B is the same for each oligonucleotide of the first population; the nucleotide sequence of B' is the same for each oligonucleotide of the second population; the nucleotide sequence of $V_1$ is variable between the oligonucleotides of the first population the nucleotide sequence of $V_2'$ is variable between the oligonucleotides of the second population, and $V_1$ and $V_2'$ hybridize to different sites in a reference genome. In some embodiments, the nucleotide sequence of B is at least 15 bases in length, the nucleotide sequences of $V_1$ and $V_2'$ are at least 25 nucleotides in length and the first and second population of oligonucleotides may comprises at least 10 oligonucleotides each. A more detailed description of the components that may be present in this composition as well as other components that may be present in the composition are described in the methods section set forth above.

Kits

Also provided by this disclosure is a kit for practicing the subject method, as described above. A subject kit may contain at least: a) a first population of oligonucleotides comprising a top strand sequence having the following formula $V_1$-B-3'; and b) a second population of oligonucleotides comprising a bottom strand sequence having the following formula: $V_2'$-B'-3', as described above. In some embodiments, the nucleotide sequences of B and B' are complementary and are at least 15 nucleotides in length; the nucleotide sequence of B is the same for each oligonucleotide of the first population; the nucleotide sequence of B' is the same for each oligonucleotide of the second population; the nucleotide sequence of $V_1$ is variable between the oligonucleotides of the first population the nucleotide sequence of $V_2'$ is variable between the oligonucleotides of the second population, and $V_1$ and $V_2'$ hybridize to different sites in a reference genome. In certain cases, the first population of oligonucleotides may comprise a top strand sequence having the following formula F-$V_1$-B-3' and the second population of oligonucleotides comprising a bottom strand sequence having the following formula R'-$V_2'$-B'-3', wherein the complements of sequences F and R' provide binding sites for forward and reverse primers. In addition, the kit may also comprise forward and reverse primers that hybridize to the complements of sequences F and R'. In certain cases, one of the forward and reverse primers may comprise a 5' phosphate or biotin. In addition, the kit may also contain reagents for performing polymerase chain assembly (e.g., polymerase, nucleotides and buffer, etc.), and other enzymes and/or reagents for performing the method, e.g., a ligase, λ exonuclease, etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The multiplex halo assay described above finds use in a variety of applications, where such applications generally include genomic DNA analysis applications in which the presence of a chromosomal rearrangement in a given sample may be detected. The subject methods may also be used to finely map chromosomal breakpoints, and other aberrations, such as micro-inversions, deletions and translocations in certain cases without a priori knowledge of their location. The subject methods find use in a variety of diagnostic and research purposes since chromosomal inversions and translocations play an important role in conditions relevant to human diseases and genomic evolution of many organisms.

In particular, the above-described methods may be employed to diagnose, or investigate various types of genetic abnormalities, cancer or other mammalian diseases, including but not limited to, leukemia; breast carcinoma; prostate cancer; Alzheimer's disease; Parkinson's disease; epilepsy; amyotrophic lateral sclerosis; multiple sclerosis; stroke; autism; Cri du chat (truncation on the short arm on chromosome 5), 1p36 deletion syndrome (loss of part of the short arm of chromosome 1), Angelman syndrome (loss of part of the long arm of chromosome 15); Prader-Willi syndrome (loss of part of the short arm of chromosome 15); acute lymphoblastic leukemia and more specifically, chronic myelogenous leukemia (translocation between chromosomes 9 and 22); Velocardiofacial syndrome (loss of part of the long arm of chromosome 22); Turner syndrome (single X chromosome); Klinefelter syndrome (an extra X chromosome); Edwards syndrome (trisomy of chromosome 18); Down syndrome (trisomy of chromosome 21); Patau syndrome (trisomy of chromosome 13); and trisomies 8, 9 and 16, which generally do not survive to birth.

The disease may be genetically inherited (germline mutation) or sporadic (somatic mutation). Many exemplary chromosomal rearrangements discussed herein are associated with and are thought to be a factor in producing these disorders. Knowing the type and the location of the chromosomal rearrangement may greatly aid the diagnosis, prognosis, and understanding of various mammalian diseases.

Certain of the above-described methods can also be used to detect diseased cells more easily than standard cytogenetic methods, which require dividing cells and require labor and time-intensive manual preparation and analysis of the slides by a technologist.

The above-described methods can also be used to compare the genomes of two biological species in order to deduce evolutionary relationships.

Genomic DNA may be isolated from a variety of sources, including tissue culture cells and mammalian subjects, e.g., human, primate, mouse or rat subjects. For example, chromosomes may be analyzed from less than five milliliters (mL) of peripheral blood. White blood cells contain chromosomes while red blood cells do not. Blood may be collected and combined with an anti-clotting agent such as sodium heparin. Genomic DNA may also be analyzed from amniotic fluid, which contains fetal cells. Such cells can be grown in tissue culture so that dividing cells are available for chromosomal analysis within 5-10 days. Genomic DNA may also be analyzed from bone marrow, which is useful for diagnosis of leukemia or other bone marrow cancers. Genomic DNA may also be analyzed from solid tissue samples. A skin or other tissue biopsy in the range of about 2-3 mm may be obtained aseptically and transferred to a sterile vial containing sterile saline or tissue transport media to provide material for chromosome analysis. Fetal tissue obtained after a miscarriage can also be used for chromosome analysis, such as from the fetal side of the placenta, the periosteum overlying the sternum or fascia above the inguinal ligament, or from chorionic villi. Fetal tissue can also be collected from multiple sites such as the kidneys, thymus, lungs, diaphragm, muscles, tendons, and gonads. An amniocentesis may also be performed.

In addition to the above, the instant methods may also be performed on bone marrow smears, blood smears, paraffin embedded tissue preparations, enzymatically dissociated tissue samples, uncultured bone marrow, uncultured amniocytes and cytospin preparations, for example.

EXAMPLES

In this example, the gene specific sequences that are to be targeted by the halo probes are identified and categorized by whether they are complementary to the 5' or 3' end of the target sequence. For those that are complementary to the 5' end, the common linker sequence is appended to the 3' end of the probe to create a chimeric sequence containing the gene specific sequence followed by the linker sequence. For those probes targeting the 3' end of the target sequence, the reverse complement of the probe sequence is generated and the reverse complement of the linker sequence is added to the 3' end.

Figure 7:
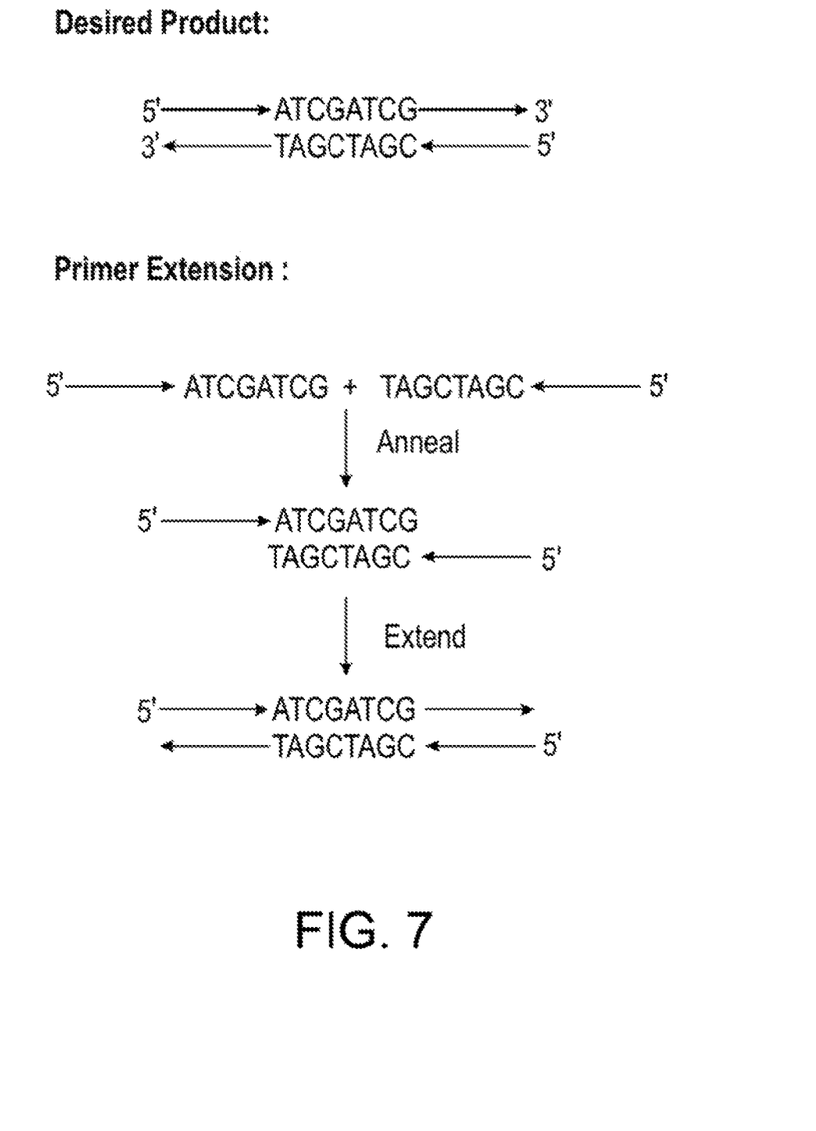
FIG. 7 shows how a halo probe can be made by primer extension.
Figure 8:
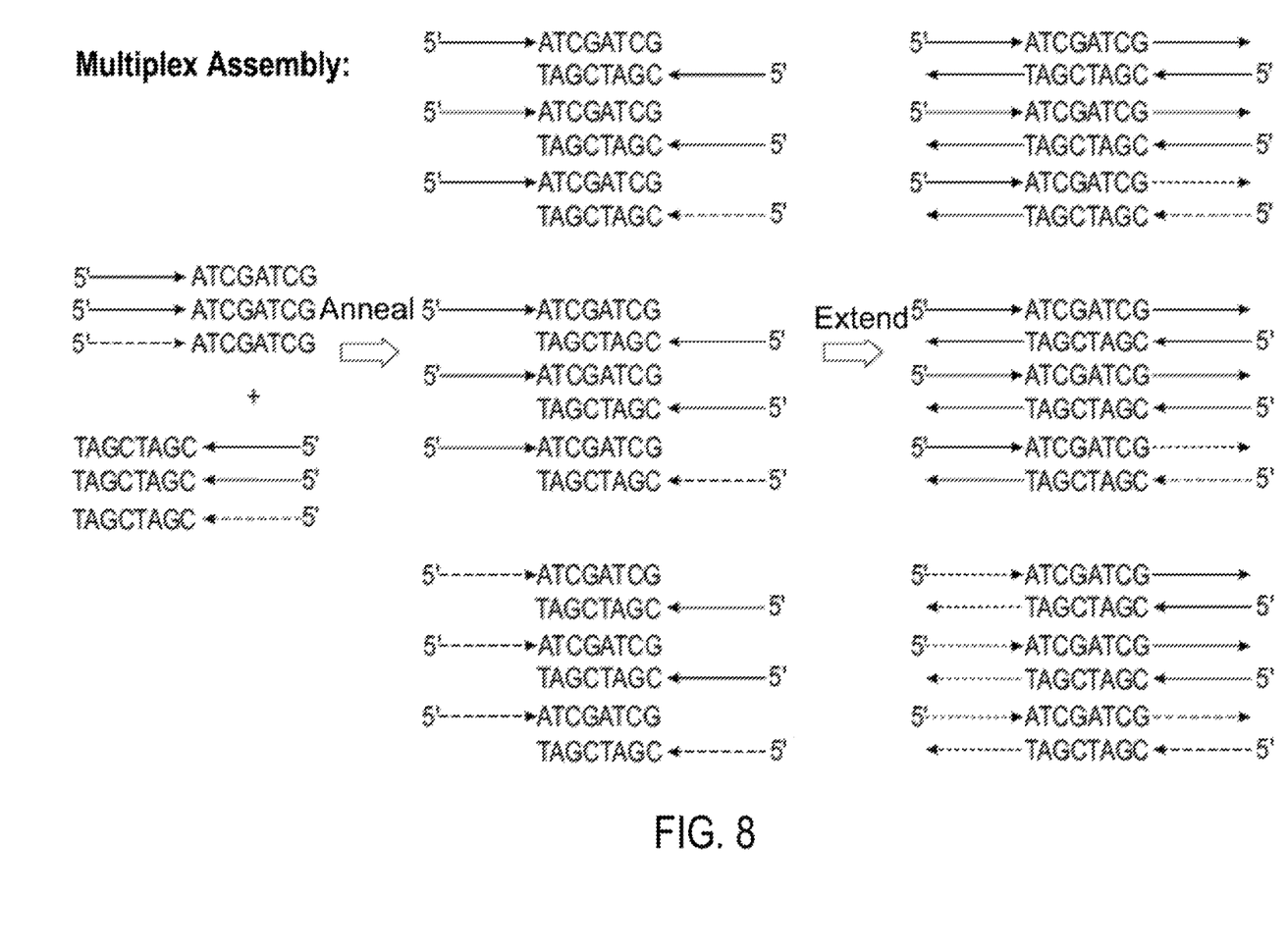
FIG. 8 shows how the general principle illustrated in FIG. 7 can be expanded to make multiple halo probes.

Each chimeric oligonucleotide is synthesized, pooled together and assembled by primer extension. The extended probes will then be selectively amplified by PCR. In using this method, the number of halo probes can be calculated by multiplying the number 5' primers used by the number of 3' primers used. For example, 10,000 Halo probes can be generated from 200 oligonucleotide synthesis reactions. FIG. 7 shows how one halo probe can be made by primer extension. FIG. 8 shows how the general principle shown in FIG. 7 can be expanded to make multiple halo probes.

The invention claimed is:

1. A method comprising:
   a) hybridizing a first population of oligonucleotides comprising a top strand sequence having the following formula:

$V_1$-B-3' with a second population of oligonucleotides comprising a bottom strand sequence having the following formula:

$V_2'$-B'-3' to provide a population of duplexes; wherein:
   the nucleotide sequences of B and B' are complementary and are at least 15 nucleotides in length;
   the nucleotide sequence of B is the same for each oligonucleotide of said first population;
   the nucleotide sequence of B' is the same for each oligonucleotide of said second population;
   the nucleotide sequence of $V_1$ is variable between the oligonucleotides of the first population;
   the nucleotide sequence of $V_2'$ is variable between the oligonucleotides of the second population, and
   $V_1$ and $V_2'$ hybridize to sites in a reference genome; and
   b) extending the 3' ends of the oligonucleotides in said duplexes to produce a population of double stranded products comprising a top strand sequence having the following formula:

$V_1$-B-$V_2$, wherein $V_2$ is complementary to $V_2'$.

2. The method of claim 1, wherein:
   said first population of oligonucleotides comprises a top strand sequence having the following formula:

F-$V_1$-B-3';

said second population of oligonucleotides comprises a bottom strand sequence having the following formula:

R'-$V_2'$-B'-3';

and said population of double-stranded products comprise a top strand sequence having the following formula:

F-$V_1$-B-$V_2$-R wherein R and the complement of F provide binding sites for forward and reverse primers.

3. The method of claim 2, further comprising:
   c) PCR amplifying said population of double-stranded products with forward and reverse primers to produce a population of PCR products, wherein the forward and reverse primers bind to R and the complement of F.

4. The method of claim 3, further comprising:

d) isolating said top strand from the bottom strand of said population of PCR products to produce a population of single stranded halo probes that hybridize to a plurality of sites in said reference genome, wherein the halo probes comprise the top strand sequence $V_1$-B-$V_2$ and one or more second oligonucleotides hybridized to the nucleotide sequence of B.

5. The method of claim 4, wherein said reverse primer is 5'-phosphorylated and said isolating is done by degrading the bottom strand of said population of double-stranded products by contacting the population of double-stranded DNA with an exonuclease.

6. The method of claim 5, wherein said exonuclease is λ exonuclease.

7. The method of claim 1, wherein said reference genome is a mammalian genome.

8. The method of claim 1, wherein the nucleotide sequence of B is at least 15 bases in length.

9. The method of claim 1, wherein the nucleotide sequences of $V_1$ and $V_2'$ are at least 25 nucleotides in length.

10. The method of claim 1, wherein said first population of oligonucleotides comprises at least 10 oligonucleotides and said second population of oligonucleotides comprises at least 10 oligonucleotides.

11. The method of claim 1, wherein the sites to which $V_1$ and $V_2$ hybridize in said reference genome each comprise a restriction site.

12. A composition of matter comprising:

a first population of oligonucleotides comprising a top strand sequence having the following formula:

$V_1$-B-3'; and a second population of oligonucleotides comprising a bottom strand sequence having the following formula:

$V_2'$-B'-3';

wherein:

the nucleotide sequences of B and B' are complementary and are at least 15 nucleotides in length;

the nucleotide sequence of B is the same for each oligonucleotide of said first population;

the nucleotide sequence of B' is the same for each oligonucleotide of said second population;

the nucleotide sequence of $V_1$ is variable between the oligonucleotides of the first population;

the nucleotide sequence of $V_2'$ is variable between the oligonucleotides of the second population;

the first and second population of oligonucleotides are capable of hybridizing to each other to produce a population of duplexes, and $V_1$ and $V_2'$ hybridize to different sites in a reference genome.

13. The composition of matter of claim 12, wherein the nucleotide sequence of B is at least 15 bases in length.

14. The composition of matter of claim 12, wherein the nucleotide sequences of $V_1$ and $V_2'$ are at least 25 nucleotides in length.

15. The composition of matter of claim 12, wherein said first population of oligonucleotides comprises at least 10 oligonucleotides and said second population of oligonucleotides comprises at least 10 oligonucleotides.

16. A kit comprising a) a first population of oligonucleotides comprising a top strand sequence having the following formula:

$V_1$-B-3'; and b) a second population of oligonucleotides comprising a bottom strand sequence having the following formula:

$V_2'$-B'-3'; wherein:

the nucleotide sequences of B and B' are complementary and are at least 15 nucleotides in length;

the nucleotide sequence of B is the same for each oligonucleotide of said first population;

the nucleotide sequence of B' is the same for each oligonucleotide of said second population;

the nucleotide sequence of $V_1$ is variable between the oligonucleotides of the first population;

the nucleotide sequence of $V_2'$ is variable between the oligonucleotides of the second population;

the first and second population of oligonucleotides are capable of hybridizing to each other to produce a population of duplexes, and $V_1$ and $V_2'$ hybridize to different sites in a reference genome.

17. The kit of claim 16, wherein the kit further comprises instructions.

18. The kit of claim 16, wherein the first population of oligonucleotides comprises a top strand sequence having the following formula:

F-$V_1$-B-3'; and and the second population of oligonucleotides comprises a bottom strand sequence having the following formula:

R'-$V_2'$-B'-3';

wherein the complements of sequences F and R' provide binding sites for forward and reverse primers.

19. The kit of claim 18, further comprising forward and reverse primers that hybridize to the complements of sequences F and R'.

20. The kit of claim 18, wherein one of said forward and reverse primers comprises a 5' phosphate or biotin.

* * * * *